United States Patent [19]
Paxton et al.

[11] Patent Number: 5,114,404
[45] Date of Patent: May 19, 1992

[54] MULTIFUNCTIONAL RETRACTABLE NEEDLE TYPE GENERAL PURPOSE DISABLING SYRINGE HAVING ENHANCED SAFETY FEATURES AND RELATED METHOD OF OPERATION

[76] Inventors: Gerald R. Paxton, 1407 S. Arcadia St., Boise, Id. 83705; Norman W. Seid, 3865 Barstow Ct.; Garry L. Gilman, 9750 Klondike Ct., both of Boise, Id. 83709

[21] Appl. No.: 557,537

[22] Filed: Jul. 24, 1990

[51] Int. Cl.⁵ .............................. A61M 5/32
[52] U.S. Cl. ..................... 604/110; 604/137
[58] Field of Search ............ 604/137, 110, 195

[56] References Cited

U.S. PATENT DOCUMENTS

| | | | |
|---|---|---|---|
| 4,188,950 | 2/1980 | Wardlaw | 604/203 |
| 4,378,015 | 3/1983 | Wardlaw | 604/137 |
| 4,826,484 | 5/1989 | Haber et al. | 604/195 |
| 4,894,005 | 1/1990 | Sudnak | 604/110 |
| 4,955,869 | 9/1990 | Bin | 604/195 |
| 4,966,593 | 10/1990 | Lennox | 604/110 |
| 4,978,340 | 12/1990 | Terrell et al. | 604/110 |
| 4,978,343 | 12/1990 | Dysarz et al. | 604/195 |
| 4,986,813 | 1/1991 | Blake et al. | 604/195 |

Primary Examiner—Paul J. Hirsch
Attorney, Agent, or Firm—William J. Bethurum

[57] ABSTRACT

A retractable needle-type syringe having a maximum amount of safety features, including maintaining the needle of the syringe in a retracted and totally shielded position prior to use. After an injection has been given, the plunger rod of the syringe can be operated by one hand of the user in such a manner as to completely and totally disable the syringe and thereby render secondary use of the syringe practically impossible. This feature leaves the other hand of the user out of danger and proximity to the syringe and available to perform other patent-assisting functions. The above multifunctional nature and operation of this invention is accomplished through the use of a minimum number individual components which are uniquely adapted for packaging and cooperative interaction within an elongated cylindrical housing of the syringe. In addition, this syringe may be manufactured in a cost-effective economical manner to produce a universal and reliable general purpose syringe having a high price-performance figure of merit.

27 Claims, 7 Drawing Sheets

MULTIFUNCTIONAL RETRACTABLE NEEDLE TYPE GENERAL PURPOSE DISABLING SYRINGE HAVING ENHANCED SAFETY FEATURES AND RELATED METHOD OF OPERATION

TECHNICAL FIELD

This invention relates generally to syringes for medical and general purpose usage and more particularly to such syringes having a retractable needle and other related and novel features. These features are directed to the safety to humans during syringe use and were heretofore unavailable in the art of medical instrumentation. These safety features have been conceived and developed to maximize the safety of the syringe user and those around him and to minimize all human exposure to the needle of the syringe when the syringe is in use. These features include the ability to completely disable the syringe after use and thereby totally prevent the possibility that the syringe be retrofitted.

BACKGROUND ART

As a result of recent increases in certain contagious diseases such as the Acquired Immune Deficiency Syndrome (AIDS), the number of cases reported where a human being has been inadvertently pricked with the needle of a syringe is growing at an alarming rate. With the current increase in these infectious diseases which may be transmitted by a contaminated syringe, this fact has caused a great concern in the medical community and other related professions not only for the health and welfare of nurses, physicians, and patients alike, but also a concern for the health and welfare of people within the illegal drug community.

Most standard types of syringes are designed so that the needle portion of the syringe is permanently in place in an extended position at the end of the syringe and there protected by a cap which is to be removed at the time the syringe is used either in the home or in hospital applications. However, an obvious disadvantage with this type of syringe construction and design (which may indeed represent the lowest cost of syringe construction) is that during the syringe handling and use by the hospital personnel and patients alike there is a relatively high degree of needle exposure to humans per unit of time that the syringe is in actual handling or use. In addition, these fixed-needle types of syringes have been known to cause needle puncture through a wall of a protective cap being replaced thereon and stick the person handling the syringe.

To reduce this human exposure time to the exposed needle, certain types of retractable-needle type syringes have been developed wherein mechanisms are provided within the syringe for withdrawing the needle to a protected and shielded position within the housing of the syringe after the syringe is actually used for giving an injection to a patient. Examples of such a retractable-needle type syringe are disclosed in U.S. Pat. No. 4,790,822 issued to Haining and in U.S. Pat. No. 4,838,869 issued to Allard, both incorporated herein by reference. However, these retractable-needle types of syringes have nevertheless failed to provide a minimum of human exposure to the needle of the syringe per unit of time when the syringe is in actual use. Furthermore, these retractable-needle type syringes have not been designed such that the syringe is disabled after use. This of course leaves open the possibility that the syringe may be retrofitted and subsequently used in such a manner to transmit an infectious disease.

Thus, these prior art devices do not minimize as completely as possible all kinds of accidental needle contacts by humans and the possible contamination of and disease contraction to a human who is inadvertently pricked by an exposed needle. With the current unfortunate increase of many contagious and infectious diseases, the desirability of reducing to an absolute minimum this quotient of human exposure-to-needle time per unit of time when a syringe is being handled and operated while simultaneously providing a totally disabling capability to the syringe is manifest.

DISCLOSURE OF INVENTION AND BRIEF DESCRIPTION THEREOF

The general purpose and principal object of the present invention is to provide a new and improved retractable-needle type of syringe whose needle exposure time per unit of time that the syringe is in actual use has been minimized with respect to any known retractable-needle type syringes of the prior art.

Another object of this invention is to provide a new and improved retractable-needle type syringe of the type described which may be rendered completely inoperative after a single injection, thereby completely eliminating the possibility of undesirable retrofitting and secondary use of the syringe for the injection of illegal drugs and the like.

Another object of this invention is to provide a new and improved retractable-needle type syringe of the type described which may be operated to provide the multiple functions of needle extension and retraction, syringe filling of fluid and ejection of fluid therefrom, and thereafter to totally disable the syringe and thus prevent the possibility of any secondary use.

Another object of this invention is to allow the syringe user to totally disable the syringe after use with a release-and-press motion of a user's thumb, thereby enabling the user's other hand to be totally removed from the syringe and "out of harm's way".

Another object of this invention is to provide a new and improved retractable-needle type syringe of the type described which is rigid and durable in construction and reliable in operation.

A novel feature of this invention is the provision of a syringe wherein the needle thereof is maintained in a retracted and totally shielded and protected position prior to the time the syringe is to be used.

Another feature of this invention is a provision of a new and improved syringe of the type described in which the above described multiple functions of needle manipulation and fluid control are performed using a novel mechanical system including certain individual parts which provide multiple functions during the five function operation of the syringe to be described in further detail below.

Another feature of this invention is the provision of a novel method of syringe operation which has now been made available in accordance with the teachings of the present invention, and by the use of a single hand of an operator to disable the syringe. This method of operation relies upon the novel co-action and cooperation of certain mechanical components which are mechanically coupled and linked within the syringe housing to thereby enable series of syringe operations to be carried out in a predetermined sequence. The syringe may then be disabled with a single release and press motion of a user's thumb, thereby not only freeing up the user's other hand to perform other functions, but also removing this other hand from the proximity of the needle during the syringe disabling operation.

These and other objects, features, and attendant advantages of this invention are accomplished by the provision of a syringe having a retractable needle movable within a syringe housing and including means for maintaining the needle in a completely retracted position within the housing prior to use, and means for driving the needle to an extended rigid and exposed position when the syringe is ready for use and for maintaining the needle in a rigid position during actual use.

This syringe described and claimed herein further includes means for retracting the needle to an inoperative position within the syringe housing once an injection is given using a simple release-and-press motion of the user's thumb.

This syringe further includes means for totally disabling the syringe once an injection has been given by removing all pressure creating and sustaining means therein.

This syringe further includes hand control means operative in response to the hand motion of a syringe operator for extending the needle, filling the syringe with fluid and giving an injection, retracting the needle into the syringe housing, and then totally disabling the syringe with a single hand motion, thereby leaving the other hand of a nurse, doctor or patient free to perform other functions during syringe use.

The novel process of operation in accordance with the present invention is directed to the method for minimizing human exposure to the needle of a syringe during handling and use and for disabling the syringe from further use after a single injection. This method comprises the steps of pressing a syringe plunger to move its associated needle to an extended and exposed position, retracting the plunger to fill the syringe with fluid, pressing the plunger forward to give an injection and simultaneously maintain the needle in an extended and rigid position, and pressing the plunger again to retract the needle into an inoperative position while simultaneously and automatically in a single motion removing all necessary pressure sustaining mechanisms within the syringe, thereby totally disabling it from further secondary use.

The above and other objects, features and various related advantages of this invention will become better understood with reference to the following description of the accompanying drawings.

BRIEF DESCRIPTION OF THE DRAWINGS

F8IG. 1 is an exploded isometric view which shows all of the syringe components physically separated one from another, but concentrically aligned in their cooperative and adjacent positions and relationships to be further described.

DETAILED DESCRIPTION OF THE PREFERRED EMBODIMENT

Figure 1:
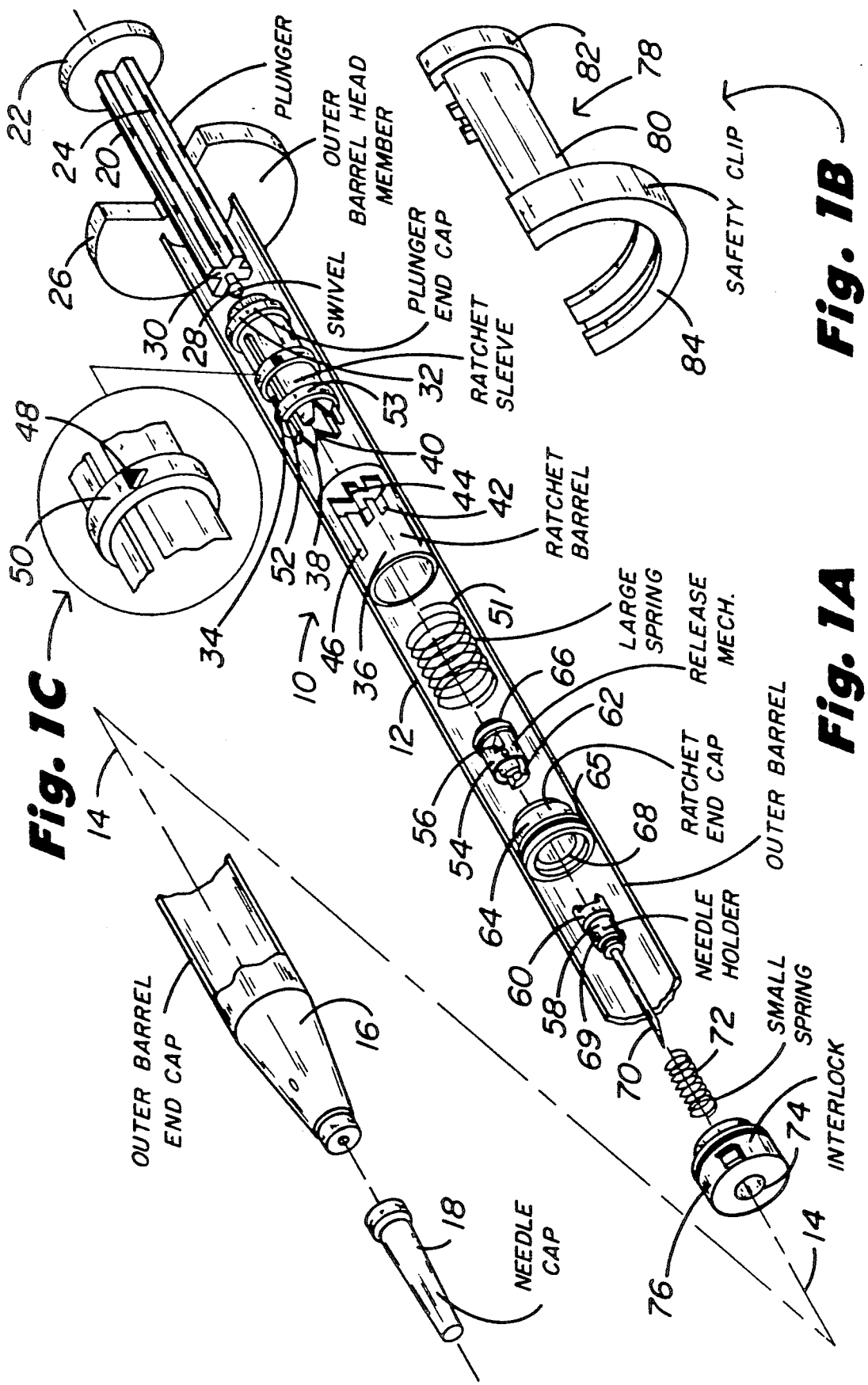
Figure 2:
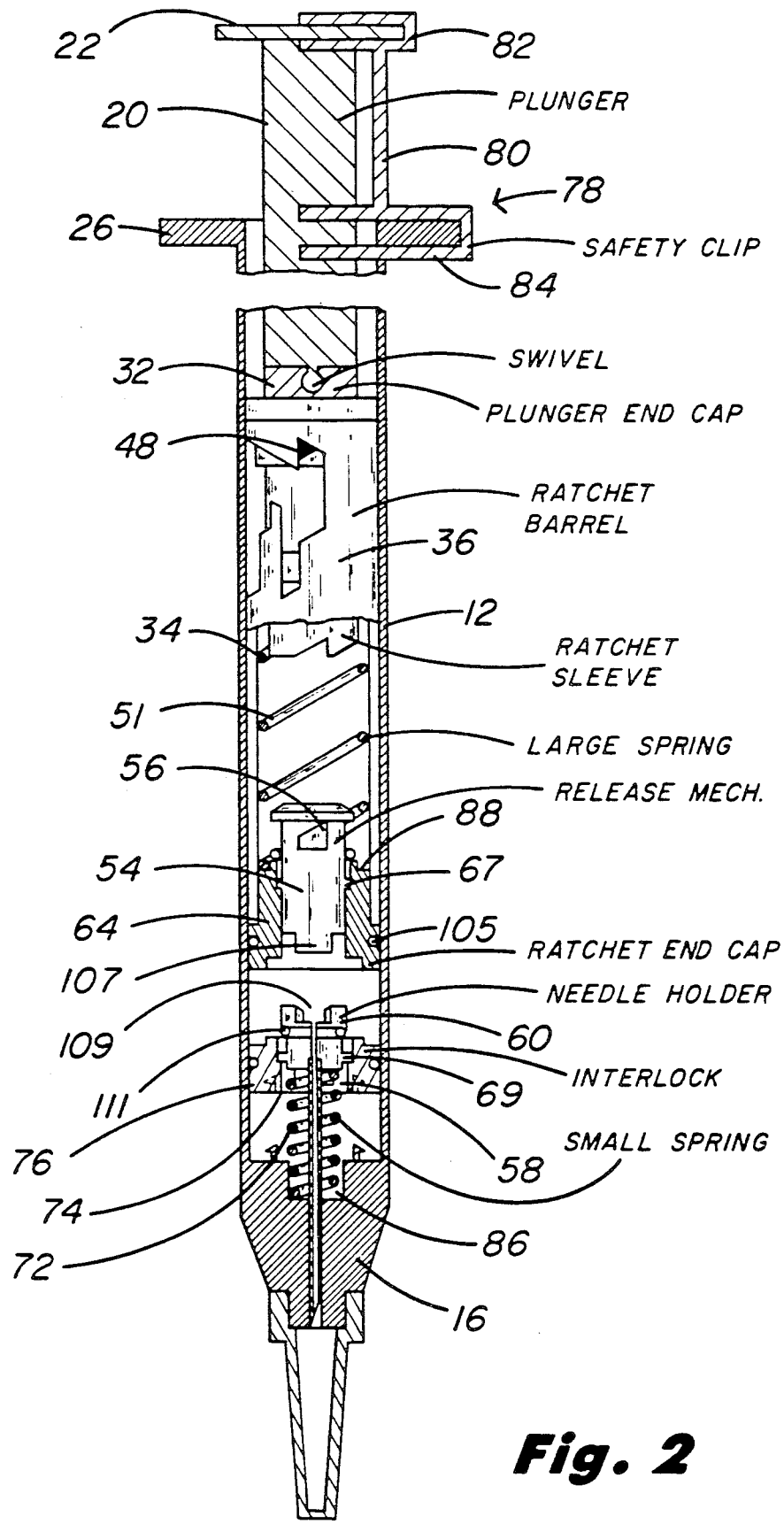
FIG. 2 is a partially sectioned and cut away isometric view of the syringe just as it is removed from a package and prior to any human contact thereto.

Referring now to FIGS. 1 and 2, the technical legend used in these figures and applied to the various components in these figures is intended to provide a good visual correlation between the description in the following specification and all of the seven figures of the drawings. In the description that follows, FIG. 1 will be described only in terms of the general identification of the syringe components and the general interrelationships between the several components shown therein. Then, the detailed operation of the preferred embodiment will be described in more functional detail with reference to FIGS. 2 through 7 which illustrate, in succession, the steps of preparing the syringe for an injection, including the fluid filling thereof, giving the injection, and then disabling the syringe from further use.

Referring again to FIG. 1, the syringe in this exploded, partially cut away isometric view is designated generally as 10 and includes an outer barrel or housing 12 in which all of the cooperative components shown are concentrically arranged along a longitudinal axis 14. The cylindrical outer barrel or housing 12 has an end cap member 16 and a removable needle cap 18 secured at one end thereof, and a plunger rod 20 having an integral plunger head member 22 extends as shown into the other end of the outer barrel or housing 12. The plunger rod 20 has four orthogonally positioned rib members 24 which slidably engage and extend through an opening in an outer barrel disk shaped head member 26, and a swivel 28 extends as shown from the cross shaped end face 30 of the plunger rod 20 and is received by a mating opening or receptacle in the plunger rod end cap 32.

The swivel 28 operates to tightly couple the end face 30 of the plunger rod 20 to an adjacent ratchet sleeve 34 at all times and to slide the ratchet sleeve up and down the outer syringe barrel or housing 12 in the manner described below. The swivel 28 allows the ratchet sleeve 34 to rotate within an outer concentric ratchet barrel 36, and during this rotation, the teeth 38 and grooves 40 of the ratchet sleeve 34 operate to control the rotation and operation of a needle release mechanism 54 of the syringe to be described. The ratchet barrel 36 has precisely configured slots or notches 42, 44, and 46 therein, and these notches operate to continuously engage and disengage a lug 48 located as shown on one side of a cylindrical band or ring 50 surrounding the outer surface of the ratchet sleeve 34.

The operation of the ratchet sleeve 34 within the ratchet barrel 36 and the movement of the lug 48 up and down within the ratchet barrel 36 and in a right-to-left rotational motion within the slots 42, 44, and 46 (as viewed in FIG. 1) represents a most significant and novel feature of the present invention and will be explained in substantial detail below. For this reason, FIG. 1 is provided with an enlarged and encircled view of a small portion of the ratchet sleeve 34 to show in expanded detail the critically operative lug 48 on the central band 50 of the ratchet sleeve 34. This lug 48 is shown as a black triangle and in the varying locations to be described in FIGS. 2-7 below.

A large spring 51 is adapted to be positioned adjacent to the cylindrical inside walls of the ratchet barrel 36 and is operatively compressed and decompressed against a facing surface 52 of another cylindrical ring or band 53 which extends around the outer cylindrical surface of the ratchet sleeve 34. The large spring 51 operates to cause the ratchet sleeve 34 to move back and forth in the ratchet barrel 36 when the user's thumb pressure is applied-released-and-applied, etc. to the head 22 of the plunger rod 20.

A release mechanism 54 having a lug 56 on each side thereof is operatively positioned as shown within the large spring 51 and within the ratchet barrel 36. The set of lugs 56 will, in operation, come to rest against the surfaces of teeth 38 and the grooves 40 within the downwardly facing end of the ratchet sleeve 34. Thus, the rotation of the ratchet sleeve 34 will in turn rotate the release mechanism 54, and the rotation of the release mechanism 54 will in turn rotate the needle holder 58 to which the release mechanism 54 is mechanically coupled. That is, the tooth and groove configuration of the head section 60 of the needle holder 58 is mated in surface configuration to the tooth and groove configuration of the projecting end section 62 of the release mechanism 54.

The release mechanism 54 extends through a cylindrical opening in a ratchet end cap 64, and the cap or head section 66 of the release mechanism 54 will come to rest on the top surface of the ratchet end cap 64. The needle holder 58 is adapted to be received through the cylindrical opening 68 of the ratchet end cap 64, and a needle 70 extends from the small end of the needle holder 58, through a small spring 72 and also through a cylindrical opening 74 of an interlock member 76.

Finally, a safety clip 78 having a cylindrical outer housing 80 extending between upper and lower ring caps 82 and 84 is constructed so that these cylindrical end caps 82 and 84 may be locked, respectively, on to the outside surfaces of the disk shaped end 22 of the plunger rod 20 and the disk shaped end 26 of the outer barrel or housing 12 of the syringe. In this manner, the safety clip 78 prevents any movement of the plunger rod 20 prior to the time it is desired to use the syringe to given an injection.

In the actual and successful reduction to practice and testing of a syringe of the type disclosed and claimed herein, the springs and needle were constructed of stainless steel, the O-ring seals were made of rubber, and the remaining parts of the syringe were constructed of injection molded plastic.

Referring now to FIG. 2, the syringe is shown in its condition ready for use, but with the safety clip 78 still in place and with the needle 70 withdrawn as shown into the outer barrel end cap 16 of the syringe. The small spring 72 in its extended position has its lower end resting in a slot 86 of the outer barrel end cap 16, and in this extended or decompressed position of the small spring 72, the interlock member 76 assumes a rest position as shown with the needle holder 58 being carried on the upper surface thereof. The large spring 51 is also in an extended or decompressed condition and extends as shown between an upper shoulder 88 of the ratchet end cap 64 and up into the ratchet barrel 36 where it surrounds the outer cylindrical surface of the ratchet sleeve 34 and assumes a rest position on the lower shoulder surface 52 of the band 53 surrounding the ratchet sleeve 34. In this position, the lug 48 is located in the middle groove 49 of the ratchet barrel 36.

Thus, the extension of the large spring 51 pushes the ratchet sleeve 34, ratchet barrel 36, and the plunger rod 20 to an extended position as shown and ready for an initial forward thrust when the safety clip 78 is removed. Thus, it should be reemphasized at this point with respect to FIG. 2 that there is no known prior art which teaches the use of a retracted needle 70 within a syringe housing 12 prior to the initial use of the syringe.

Figure 3:
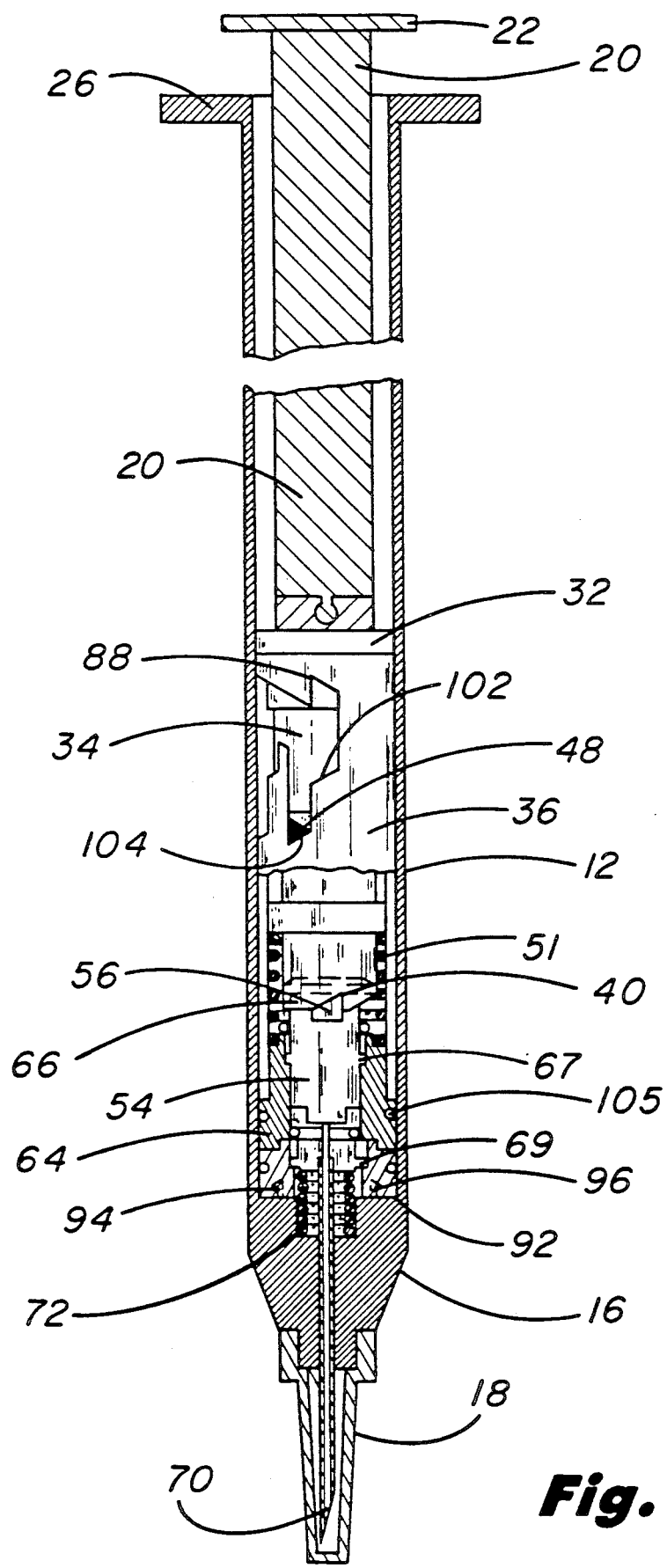
FIG. 3 is a partially sectioned and cut away isometric view which illustrates the initial forward motion of the plunger of the syringe used to lock the needle securely in place in an extended position within the syringe end cap.

Referring now to FIG. 3, this figure shows the change in relative positions of the above identified syringe components when the plunger rod 20 is thrust inwardly of the syringe housing 12 and in a downwardly direction as viewed in this figure. Since the plunger end cap 32 is locked onto the top end of the ratchet barrel 36, and since the friction of the O-ring seal 105 and the interlock of the lug 56 and groove 40 maintain the ratchet band 36 fixed in place against rotation, the ratchet barrel 36 cannot rotate as the plunger rod 20 forces it down into the syringe housing 12. The initial inward thrust of the plunger rod 20 causes the lug 48 to move downwardly first to the slanted surface 102 of the ratchet barrel 36 and then on down into the central slot 104 of the ratchet barrel 36. During this motion, the ratchet sleeve 34 is thrust down over the end cap 36 of the release mechanism 54. Additionally, during this action, the groove 40 in the ratchet sleeve 34 engages the set of lugs 56 on the outer wall of the release mechanism 54. This action in turn drives the release mechanism 54 and the ratchet end cap 64 downwardly within the syringe housing 12 to the position shown in FIG. 3.

The release mechanism 54 and the ratchet end cap 64 are initially locked in place by the lug 67, so these two pieces 54 and 64 are forced down together by the thrust of the plunger rod 20. Similarly, the needle holder 58 and the interlock 76 are initially locked into place by the lug 69, so these latter two pieces move down together to come to rest on the inner shoulder 92 of the outer barrel end cap 16. This action in turn locks the needle 70 securely in place in its extended position as shown ready for insertion into a liquid container for filling the syringe 10 with a chosen medication 100 for injection.

Figure 4:
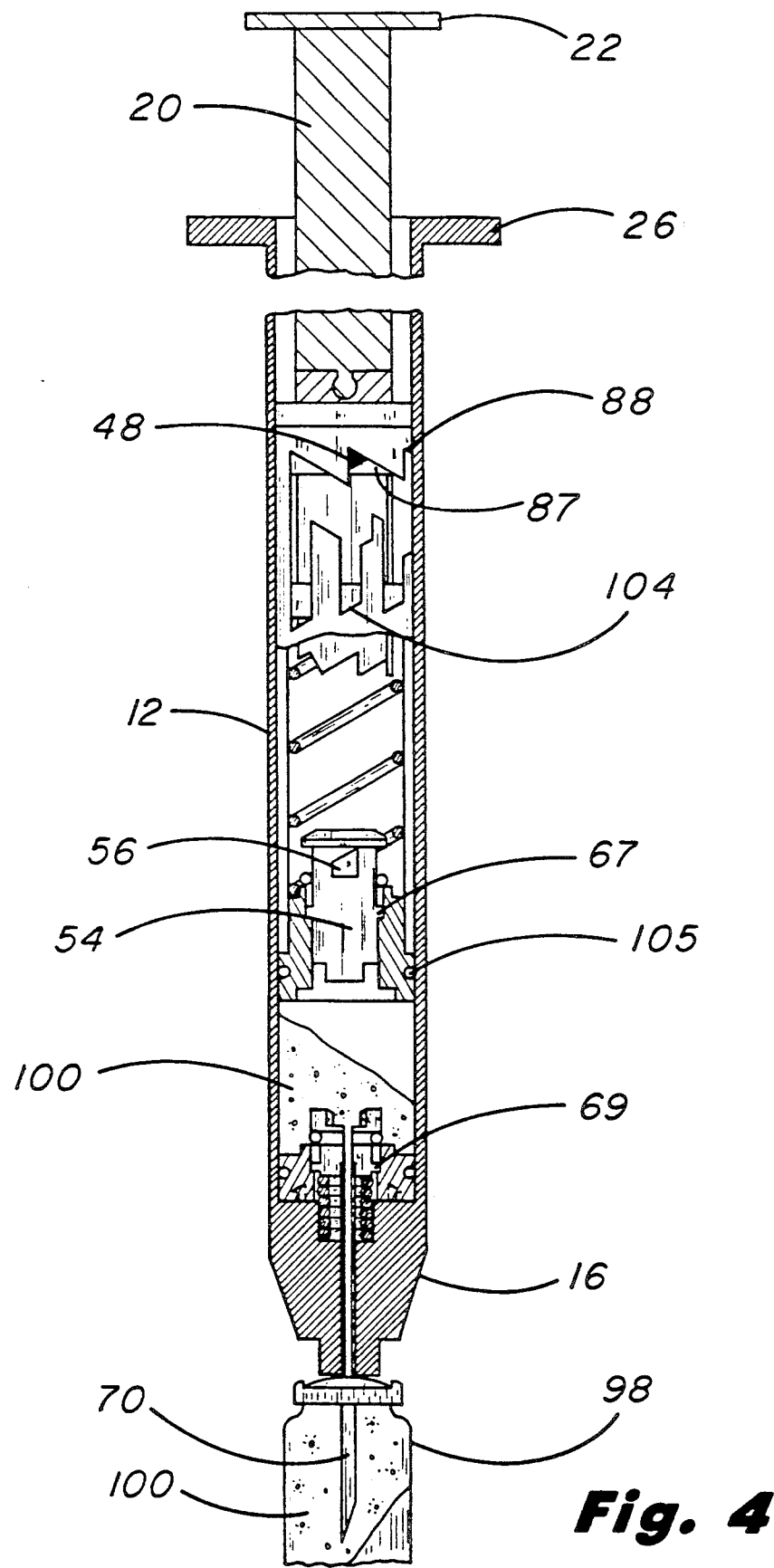
FIG. 4 is a partially sectioned and cut away isometric view showing the syringe end cap removed, the needle inserted into a liquid container and the syringe plunger being retracted to fill the syringe with a fluid to be injected.

Referring now to FIGS. 3 and 4, when the needle 70 has been inserted into a liquid container 98 having a liquid medication 100 therein, the plunger rod 20 is retracted back up the outer barrel 12 of the syringe 10, pulling with it the ratchet sleeve 34 and the ratchet barrel 36. During this retractive motion, the lug 48 on the ratchet sleeve 34 disengages the notch 104 as shown in FIG. 3, moves upwardly and then slides across the slanted surface 87 of the ratchet barrel 36 and up into the next adjacent V-shaped groove 88 of the ratchet barrel 36. This action causes the ratchet sleeve 34 to rotate by one vertical notch around the longitudinal axis 14 of the syringe 10. The lug 48 now working against the groove 88 of the ratchet barrel 36 causes the ratchet barrel to move upwardly in the syringe housing 12, and at the same time the ratchet sleeve 34 disengages the lug 56 on the release mechanism 54. However, the ratchet end cap 64 remains locked into place around the outer surface of the release mechanism 54, and the large spring 51 working against the ratchet end cap 64 pulls the ratchet end cap 64 and release mechanism 54 upwardly within the syringe outer barrel 12. During this motion, the O-ring seal 105 of the ratchet end cap 64 is pressed tightly against the inside walls of the syringe barrel or housing 12 to create a partial vacuum within the syringe housing and of sufficient backpressure to pull the liquid 100 from the container 98 and through the needle 70 and into the interior cylindrical opening within the syringe housing 12. Since the large spring 51 is tightly coupled to the ratchet sleeve 34 and pulled up around one of the outer bands 53 thereof, the retraction of the ratchet sleeve 34 upwardly in the syringe housing will also pull the large spring 51 upwardly within the syringe housing, bringing with it the ratchet end cap member 64 to which the large spring is also tightly coupled.

Figure 5:
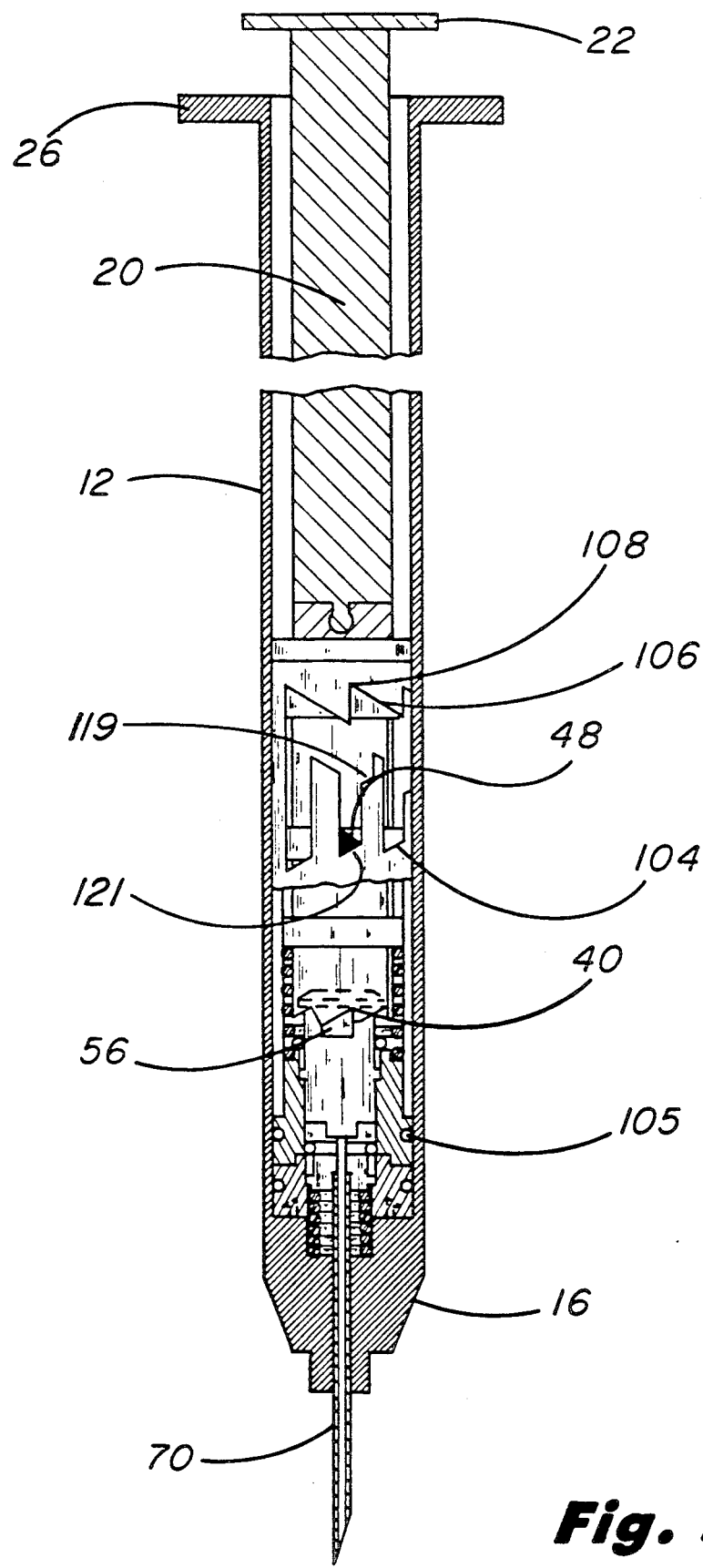
FIG. 5 is a partially sectioned and cut away isometric view which again illustrates the forward motion of the syringe plunger when a shot or injection is given to a patient.

Referring now to FIG. 5, this figure depicts the shot or injection being given, and in this motion the lug 48 on the ratchet sleeve 34 is moved out of the groove 88 in the ratchet barrel 36, then vertically downward and against the slanted surface 106 of the ratchet barrel 36 and then down into the bottom of the groove 121, thereby again causing the ratchet sleeve 34 to rotate from right to left another notch as viewed in FIG. 5. With the lug 48 locked into the groove 121 of the ratchet barrel 36, the downward thrust of the plunger rod 20 against the plunger end cap 32 and its pushing against the ratchet sleeve 34 forces the ratchet barrel 36 in a downwardly direction within the syringe housing 12 to in turn force all of the medication liquid out of the needle 70 and into the patient. During this motion, the lugs 56 on the opposite sidewalls of the release mechanism 54 again engage opposing grooves 40 on opposite sides of the ratchet sleeve 34.

Figure 6:
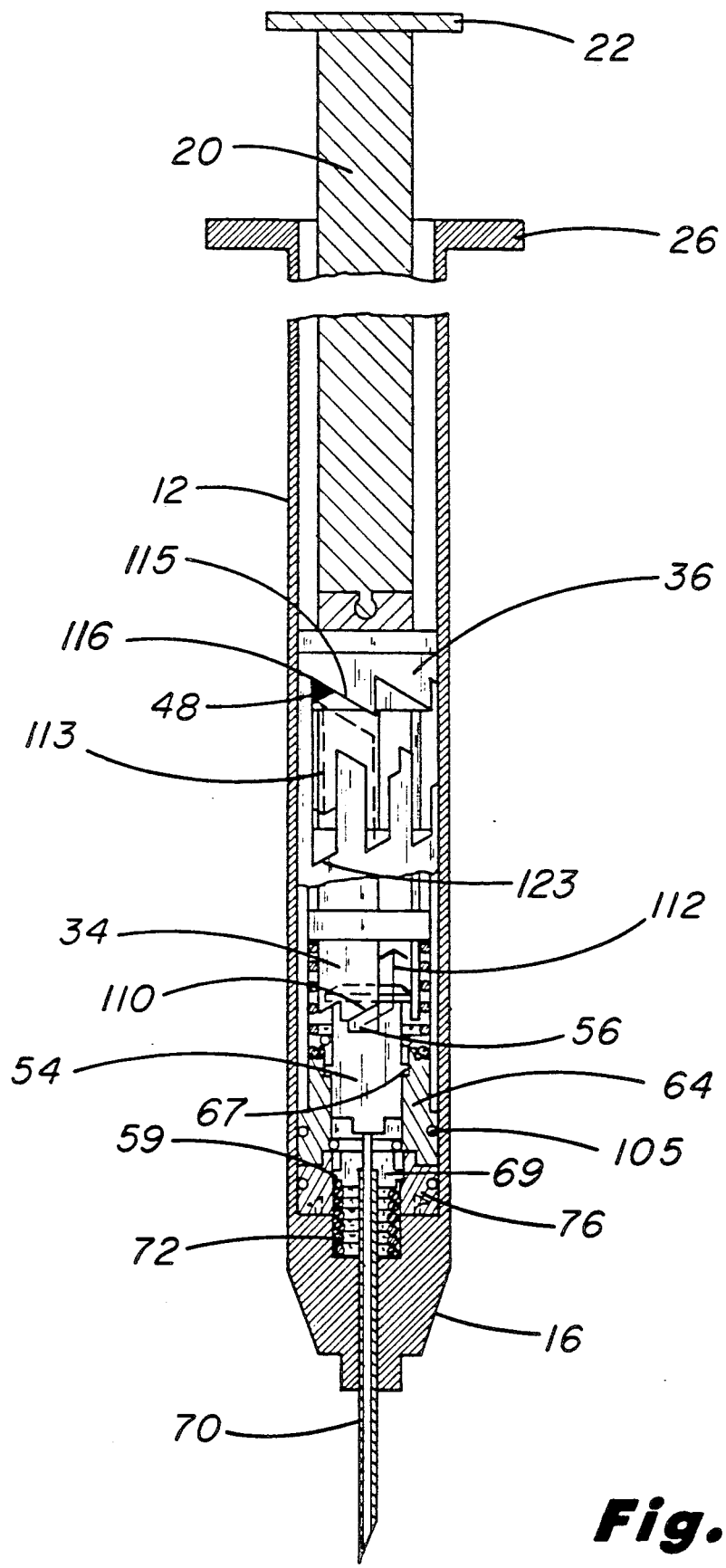
FIG. 6 is a partially sectioned and cut away isometric view illustrating the retracting motion to the syringe's release mechanism and in turn produced by the rotation of the ratchet sleeve within the ratchet barrel of the syringe to be described herein.

Referring now to FIG. 6, the partially cut away cross section view of the syringe 10 shown in this figure illustrates the upward motion of the plunger rod 20 which starts the disabling action of the syringe, the needle and the needle holder therein. During the upward motion of the plunger rod 20 in FIG. 6, the lug 48 on the ratchet sleeve 34 is again moved upwardly by the expansion of the large spring 51 and in the direction of the upward arrow 113 and then to the left and along the slanted notch surface 115 defining the notch 116, and then into the next adjacent notch 116 of the ratchet barrel 36. During this time, the ratchet sleeve 34 again rotates from right to left as viewed in FIG. 6 to now bring a slanted tooth surface 110 of the ratchet sleeve 34 into contact with the two lugs 56 on the release mechanism 54. The tooth surface 110 is adjacent to a specially operative and critical long slot 112 extending vertically as shown in the ratchet sleeve 34. When the lugs 56 are driven against the slanted surface 110 on the outer cylindrical housing of the ratchet sleeve 34, the release mechanism 54 is rotated from left to right and in turn rotates lugs 69 on needle holder 58 into a position inside of interlock 76 as viewed in FIG. 6. Now the two lugs 56 and 69 are now free to follow the direction of the arrow 112 as indicated in FIG. 6, pass vertically upward in the syringe housing 12 and allow the release mechanism 54 to be forced by the natural expansion of the small spring 72 upwardly into the inside of the ratchet sleeve 34.

Referring again to FIG. 6, it is most important to note that the lug 48 moves upwardly from its previous slot position 121 in FIG. 5 and into its new slot position 116 merely by the working of the expanding large spring 51 against the ratchet sleeve 34 when a thumb or finger is removed from the head 22 of the plunger rod 20. Thus, the head 22 of the plunger rod 20 will move upwardly from the position shown in FIG. 5 to the position shown in FIG. 6, which is a distance typically on the order of 1-3 inches. This is a distance range within which a syringe user will typically raise a thumb above the plunger head 22 after an injection is given to allow the syringe to now load itself for the next and final disabling plunger rod motion without the syringe ever leaving the user's hand or requiring the user's other hand for assistance in syringe operation. Now, with the user's thumb in a raised position above the plunger head 22 in FIG. 6, the thumb may now press the plunger rod 20 in a downwardly direction to thereby move the lug 48 in the direction of the arrow 117 and then to rest within its final slot or slot position 123 as shown in FIG. 7.

Figure 7:
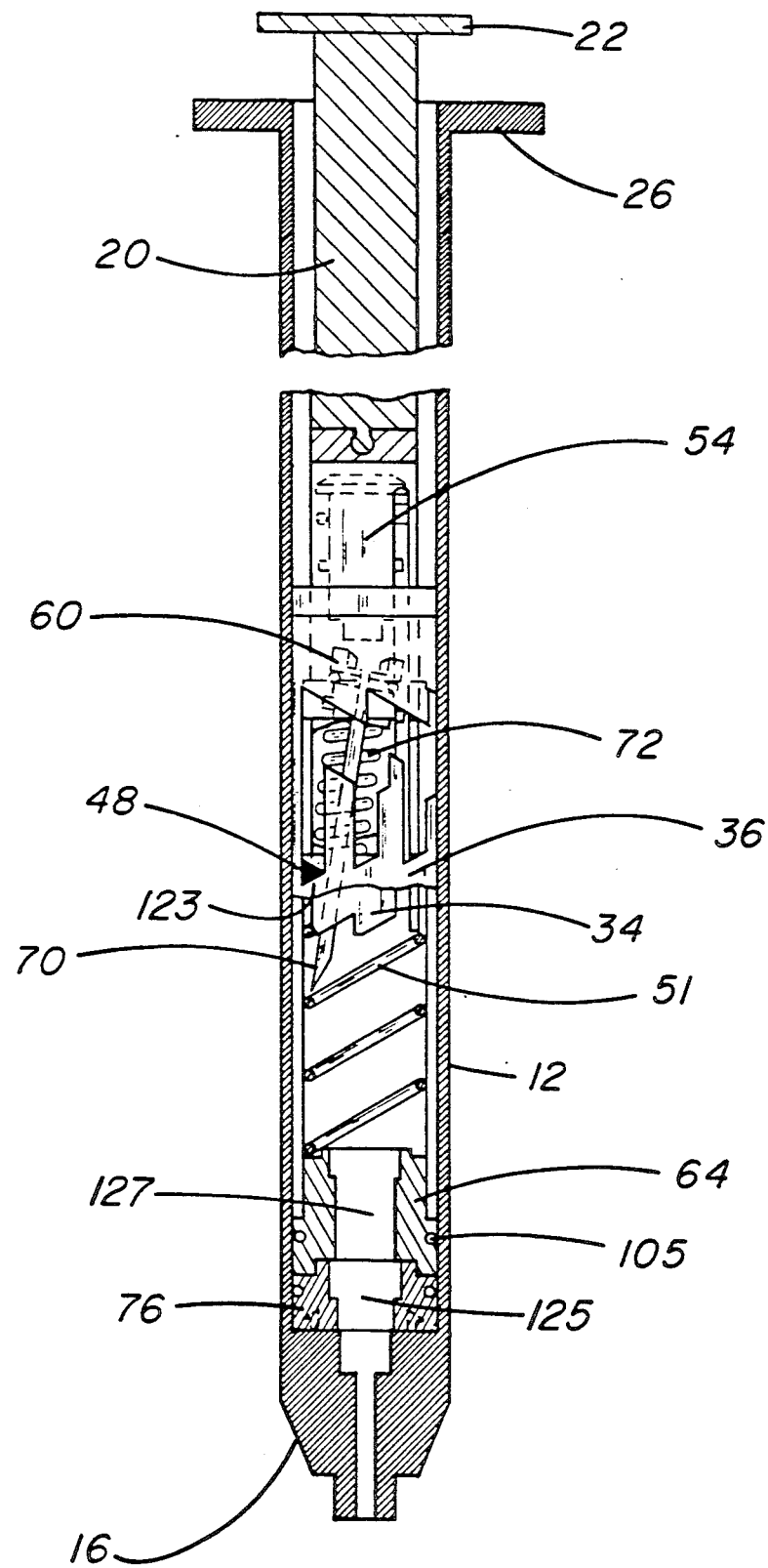
FIG. 7 is as partially sectioned and cut away isometric view which illustrates the retracting and disabling motion to the syringe components which pulls the needle to an inaccessible and disabled position within the syringe housing. This motion simultaneously removes all pressure within the syringe housing, thereby making it practically impossible to again fill the syringe with fluid or utilize the needle thereof.

Referring now to FIG. 7, this retraction of the release mechanism 54 into the syringe housing 12 is shown in final detail, and the removal of the release mechanism 54 from the grooved head 60 of the needle holder 58 allows the small spring 72 to work against the lower shoulder of the head 60 of the needle holder 58 and thereby force the needle holder 58 back up into the syringe housing 12. Here the needle 70 is shown partially in a dotted line representation within the retracted coil spring 72 which, by its natural free spring decompressed motion, will have a tendency to spring up into the syringe housing 12 to the position indicated in the cut away portion of FIG. 7. During this motion, not only are the needle and needle holder 70 and 58 retracted back into the syringe housing 12 to the partially cut-away and dotted-line totally disabled position as shown in FIG. 7, but simultaneously with this retraction motion, all vacuum within the syringe housing is removed. This takes place when the needle holder 58 and the release mechanism 34 move upwardly out of the openings 125 and 127, respectively, and allow air to pass through these openings and thereby remove all pressure from the interior of the syringe housing 12. Thus, not only is the needle 70 wholly inaccessible to the would-be secondary user, but the syringe itself is now totally incapable of creating any back or forward pressure therein necessary for injecting fluid therein or ejecting fluid therefrom.

Various design modifications may be made in and to the above described preferred embodiment without departing from the spirit and scope of this invention. For example, it may be desirable to use elliptical plunger-to-housing configurations to ensure that rotation is prevented by all of the above-described cylindrical components of the syringe. Furthermore, it may be desirable in accordance with other syringe applications to arrange the ratchet action described herein to make the syringe and needle operable for multiple injections, such as in the immunization of animals, before activating the above described disabling mechanisms to render the syringe inoperable. Accordingly, it should be understood that such design modifications and other application-specific syringe modifications are clearly within the scope of the following appended claims.

We claim:

1. A syringe of the type having a retracted needle movable within a syringe housing and therein protected and shielded prior to syringe use including, in combination:
   a. means for maintaining said needle in a completely retracted position within said housing prior to use, and
   b. plunger means mechanically coupled between one end of said syringe where it is exposed to pressing by a finger or thumb at one end of said needle for driving said needle to an extended and exposed position when said syringe is ready for use, whereby said syringe may be operated with one hand of a user.

2. The apparatus defined in claim 1 which further includes means for retracting said needle to an inoperative position within said syringe housing once an injection has been given.

3. The apparatus defined in claim 1 which further includes means for totally disabling said syringe once an injection is given by removing all pressure creating and sustaining means therein.

4. The apparatus defined in claim 2 which further includes means for simultaneously disabling said syringe during said needle retraction by removing all pressure creating and sustaining means therein.

5. The apparatus defined in claim 4 which further includes hand control means operative in response to the single handed control of a syringe operator during the needle extension, retraction, and disabling thereof with a single hand motion, thereby leaving the other hand of a syringe operator free for performing other functions and remote from danger of being inadvertently struck with a needle.

6. The apparatus defined in claim 5 wherein said hand control means includes a plunger rod operative to rotate and drive a rachet gear during its back and forth motion, whereby said rachet gear is operative during controlled rotation to control other position control and release mechanisms within said syringe housing.

7. The apparatus defined in claim 6 which includes a ratchet sleeve and ratchet barrel mechanically coupled to said driving means for producing controlled rotational motion within a housing of said syringe and thereby maintaining said needle in an extended rigid position while said syringe is in use, and thereafter providing retracting motion to said needle to render said needle inaccessible within said syringe housing and removing all pressure therefrom after an initial use of said syringe.

8. The apparatus defined in claim 7 which further includes a release mechanism operatively coupled between said needle and said ratchet sleeve and ratchet barrel for rotating to a predetermined release position adjacent to said ratchet sleeve and releasing said needle into said syringe housing after the initial use of said syringe.

9. The apparatus defined in claim 8 which further includes interlock means mechanically coupled between said release mechanism and said needle for locking said needle into a fixed rigid position while in use.

10. A syringe which may be totally disabled after an initial use so that it cannot be retrofitted which comprises means within a syringe housing and mechanically coupled to a needle holder therein for retracting said needle holder and needle attached thereto into said housing after an initial syringe use while simultaneously removing all pressure sustaining means within said housing.

11. The syringe defined in claim 10 which further includes:
   a. means for maintaining said needle in a completely retracted position within said housing prior to use, and
   b. means for driving said needle to an extended and exposed position when said syringe is ready for use.

12. The syringe defined in claim 11 which further includes hand control means operative in response to the single handed control of a syringe operator during the needle extension, retraction, and disabling thereof with a single hand motion, thereby leaving the other hand of a syringe operator free for performing other functions and out of danger of being contaminated by said needle.

13. The syringe defined in claim 12 wherein said hand control means includes a plunger rod operative to rotate and drive a rachet gear during its back and forth motion, whereby said rachet gear is operative during controlled rotation to control other position control and release mechanisms within said syringe housing.

14. The syringe defined in claim 13 which includes a ratchet sleeve and ratchet barrel mechanically coupled to said driving means for producing controlled rotational motion within a housing of said syringe and thereby maintaining said needle in an extended rigid position while said syringe is in use, and thereafter providing retracting motion to said needle to render said needle inaccessible within said syringe housing and removing all pressure therefrom after an initial use of said syringe.

15. The syringe defined in claim 14 which further includes a release mechanism operatively coupled between said needle and said ratchet sleeve and ratchet barrel for rotating to a predetermined release position adjacent to said ratchet sleeve and releasing said needle into said syringe housing after the initial use of said syringe.

16. The syringe defined in claim 15 which further includes interlock means mechanically coupled between said release mechanism and said needle for locking said needle into a fixed rigid position while in use.

17. A non-retrofittable syringe including ratchet rotation means within a syringe housing and mechanically coupled between a plunger rod and a needle holder and operative to initially drive said needle to a non-shielded position in preparation for an injection and thereafter operative to retract said needle into said syringe housing to a totally inoperative and disabled position therein.

18. The syringe defined in claim 17 which includes a ratchet sleeve and ratchet barrel mechanically coupled between said plunger rod and needle holder for producing controlled rotational motion within a housing of said syringe and thereby maintaining said needle in an extended rigid position while said syringe is in use, and thereafter providing retracting motion to said needle to render said needle inaccessible within said syringe housing and removing all pressure therefrom after an initial use of said syringe.

19. The syringe defined in claim 18 which further includes a release mechanism operatively coupled between said needle and said ratchet sleeve and ratchet barrel for rotating to a predetermined release position adjacent to said ratchet sleeve and releasing said needle into said syringe housing after the initial use of said syringe.

20. The syringe defined in claim 19 which further includes interlock means mechanically coupled between said release mechanism and said needle for locking said needle into a fixed rigid position while in use.

21. A retractable needle type syringe including a plunger rod mechanically coupled through a syringe housing to a needle, including: means mechanically coupled between said plunger rod and said needle and rotationally responsive to an inwardly press of said plunger rod into said housing for retracting said needle to an inoperative position within said housing, whereby a slight thumb or finger motion acting against an end of said plunger rod is operative to disable said syringe, thereby leaving the other hand of said user available for other functions and out of harm's way.

22. The syringe defined in claim 21 wherein said mechanically coupled means further includes:
   a. means for extending said needle from the end of said syringe housing when ready for use,
   b. means for retracting said plunger rod to limited but extended position when thumb or finger pressure is removed from said plunger rod, and
   c. means coupled to said plunger rod and responsive to the thumb or finger press against the end of said plunger rod for releasing pressure on said needle and retracting said needle back into said housing.

23. The syringe defined in claim 22 wherein said releasing and retracting means in paragraph (c) includes an inner ratchet sleeve means working rotationally against and outer ratchet barrel means.

24. A method for operating a syringe which includes the steps of:
   a. pressing a plunger rod forward to extend a needle therefrom, and
   b. pressing said plunger rod forward after an injection has been given to retract said needle in a housing of said syringe to disable said syringe.

25. The method defined in claim 24 which further includes:
   a. providing ratchet rotational control of mechanical components operatively arranged between said plunger rod and said needle, and
   b. maintaining said needle in a retracted and shielded position within said syringe housing prior to syringe use.

26. A method for minimizing human exposure to the needle of a syringe and for totally disabling said syringe from further use after a single injection which comprises the steps of:
   a. pressing a syringe plunger to move a needle thereof from a shielded position into an extended and exposed position,
   b. retracting said plunger to fill said syringe with a fluid,
   c. pressing said plunger forward to give an injection and maintain said needle in an extended and rigid position,
   d. pressing said plunger to retract said needle into said syringe housing and into an inoperative position and condition, while also simultaneously
   e. removing all pressure sustaining means from said syringe and preventing any fluid from being drawn therein or ejected therefrom.

27. The method defined in claim 26 which includes providing ratchet rotation of components to thereby provide needle thrust motion to insure rigid placement of said needle when said needle is in use and thereafter utilizing the same general ratchet rotational motion to release said needle back into the housing of said syringe and disable same from any further use.

* * * * *